US00PP12368P2

(12) United States Plant Patent
Utecht

(10) Patent No.: US PP12,368 P2
(45) Date of Patent: Jan. 22, 2002

(54) GERANIUM PLANT NAMED 'FISPURPLE'

(75) Inventor: Angelika Utecht, Montabaur (DE)

(73) Assignee: Florfis AG, Binningen (CH)

( * ) Notice: Subject to any disclaimer, the term of this patent is extended or adjusted under 35 U.S.C. 154(b) by 0 days.

(21) Appl. No.: 09/631,974

(22) Filed: Aug. 3, 2000

(51) Int. Cl.[7] ..... A01H 5/00
(52) U.S. Cl. ..... Plt./329
(58) Field of Search ..... Plt./329, 325

(56) References Cited

PUBLICATIONS

Fischer Selections 1999/2000 Catalogue featuring Magic 99 ('Fispurple').
Swiss Application for 'Fispurple' (Apr. 22, 1999).
European Union Application for 'Fispurple' (Aug. 17, 1998).
European Union Grant for 'Fispurple' (Aug. 16, 1999).
German Application for 'Fispurple' (Aug. 15, 1997).
German Denomination for 'Fispurple' (Jul. 15, 1998).
German Grant for 'Fispurple' (Jan. 15, 1999).
GTITM UPOVROM Citation for 'Fispurple' as per QZ PBR 980822; Jun. 15, 1998.*
GTITM UPOVROM Citation for 'Fispurple' as per PL PBR PE00092; Dec. 1, 1998.*

* cited by examiner

*Primary Examiner*—Bruce R. Campell
*Assistant Examiner*—Kent L. Bell
(74) *Attorney, Agent, or Firm*—Foley & Lardner

(57) ABSTRACT

A new and distinct cultivar of geranium plant named 'Fispurple', as described and illustrated, and particularly characterized by the combined features of small, round, intense purple-red colored flowers, compact inflorescence, medium-green foliage with slight zonation, and compact, lowly molded plant habit.

1 Drawing Sheet

BACKGROUND OF THE INVENTION

The present invention relates to a new and distinct cultivar of geranium plant, botanically known as *Pelargonium zonale,* and hereinafter referred to by the cultivar name 'Fispurple'.

'Fispurple' is a product of a planned breeding program which had the objective of creating new geranium varieties with purple to cherry-red flower color and relatively compact plant habit.

'Fispurple' originates from spontaneous seed set of the variety 'Robe' (unpatented), discovered in Galdar, Gran Canaria, Spain, in 1992 by the inventor, Angelika Utecht. The commercial variety 'Robe' is characterized by dark-red to purple-red, semi-double flowers, medium-green foliage with weak zonation and compact plant habit.

'Fispurple' was selected as one flowering plant within the progeny of the stated seed set by the inventor, Angelika Utecht, in 1993 in a controlled environment in Galdar, Gran Canaria, Spain.

The first act of asexual reproduction of 'Fispurple' was accomplished when vegetative cuttings were taken from the initial selection in autumn 1993 in a controlled environment in Galdar, Gran Canaria, Spain, by, or under the supervision of, Angelika Utecht. Horticultural examination of plants grown from cuttings of the plant, initiated in May 1996, in Hillscheid, Germany, and continuing thereafter, has demonstrated that the combination of characteristics as herein disclosed for 'Fispurple' are firmly fixed and are retained through successive generations of asexual reproduction.

BRIEF DESCRIPTION OF THE INVENTION

The following traits have been repeatedly observed and are determined to be basic characteristics of 'Fispurple', which in combination distinguish this geranium as a new and distinct cultivar:

1. Brilliant purple-red colored, round, semi-double flowers;
2. Medium to large, tight, nearly semi-spherically shaped umbels;
3. Medium-green foliage with weak zonation;
4. Relatively compact, low, but wide, plant habit; and
5. Mid-season spring flowering response.

'Fispurple' has not been observed under all possible environmental conditions. The phenotype of the new cultivar may vary significantly with variations in environment such as temperature, light intensity and day length without any change in the genotype. The following observations, measurements, and comparisons describe plants grown in Hillscheid, Germany, and in Langley, British Columbia, Canada, under greenhouse conditions which approximate those generally used in commercial practice.

Of the many commercial cultivars known to the present inventor, the most similar in comparison to 'Fispurple' are the variety 'Fismag' (U.S. Plant Pat. No. 8,725) and the parental variety 'Robe'. In comparison to 'Fismag', 'Fispurple' has smaller and more round-shaped flowers with a distinctly more intense and more bluish tone of color. Furthermore, 'Fispurple' grows less vigorously and remains relatively low and compact, while 'Fismag' tends to develop a tall and somewhat more open plant habit during the summer.

In comparison to 'Robe', 'Fispurple' has a more purple-red tone of flower color, in contrast to the deep cherry-red of 'Robe', and somewhat more intense green color of foliage, zonation and sepals.

BRIEF DESCRIPTION OF THE DRAWING

The accompanying photographic illustration shows typical flower and foliage characteristics of 'Fispurple' with colors being as true as possible with an illustration of this type.

DETAILED BOTANICAL DESCRIPTION

The measurements were taken in Langley, British Columbia, Canada, on Jun. 15, 1999, 12 weeks after planting of rooted cuttings into 15-cm pots. The plants had not been pinched. In the following description, color references are made to The Royal Horticultural Society (R.H.S.) Colour Chart. The color values were determined indoors from plants developed in a greenhouse in May 1999 in Hillscheid, Germany.

Classification:

*Botanical.*—A hybrid of the species *Pelargonium zonale L'Hérit.*

*Commercial.*—Zonal geranium, cv. 'Fispurple'.

Inflorescence:

*Umbel.*—Shape: Compact, nearly semi-spherical. Average diameter: 95 mm. Average depth: 45 mm. Peduncle length: 141 mm. Peduncle color: Light-green, about RHS 144 A. Pedicel length: 22 mm. Pedicel color: Upper part is red to dark-red, near RHS 60 A; the base is green RHS 143 B. Number of flowers per umbel: About 20–30. Lastingness of the umbel: Approximately 20 days at 18° C.

*Corolla.*—Average diameter: 46 mm. Form: Semi-double. Shape: Nearly round, cup-shaped. Number of petals: 9–10. Size: Upper petals (2) are 24–26 mm long, 17–20 mm wide; lower petals are approximately 23 mm long and 20 mm wide; inner petals are smaller. Shape: Obovate, attenuate base, upper end is rounded, margin entire or with very slight crenation at the tip. Number of petaloids: 0–2. Color of petaloids: Upper and lower surface RHS 57 A, base is whitish to pale pink RHS 65 D. Color (general tonality from a distance of three meters): Intense purple-red. Color of upper petals: RHS 57 A. Markings of upper petals: Scarlet zone at the base, near RHS 44 A. Color of lower petals: RHS 66 A. Color of lower surface of petals: Upper petals RHS 52 A, lower petals RHS 57 A. Color of sepals: Outer surface green, varying between RHS 143 A to RHS 143 B, with reddish base RHS 185 B, inner surface light green RHS 143 C, with reddish base RHS 47 A. Number of sepals: 5. Size of sepals: 10–12 mm long, 4–5 mm wide for the largest upper sepal; 3 mm wide for the other sepals. Shape of sepals: Linear to lanceolate; acute tip; truncate base; surface with weak, short pubescence; margin entire.

*Bud (just before petals unfold).*—Shape: Elliptical to broad elliptical. Color (sepals): Mainly light-green, RHS 143 B, reddish at the base RHS 179 A. Color (petals): Intense red, about RHS 57 A. Length: 14–16 mm. Width: 10 mm.

*Reproductive organs.*—Androecium: About 5 fertile anthers with whitish filaments and yellow-orange pollen, RHS 33 A in moderate amount. Gynoecium: 5–6-lobed stigma, purple-red stigma and filament, one pistil per flower. Fertility/seed set: Occasionally, a few seeds are developed, oblong shape, 4–5 mm long, brown RHS 177 B. Fruit: Oblong, 6 mm long.

*Spring flowering response period.*—In Hillscheid, Germany, in 1999, plants had on average 0.6 flowers opened 8 weeks after planting of rooted cuttings.

*Outdoor flower production.*—Medium to rich, the flower count in 1999, in Hillscheid, Germany, indicated about 3.5 inflorescences per plant in mid-May.

*Durability.*—Good shatter resistance and relatively good rain resistance.

*Lastingness of the individual bloom.*—Approximately 8 days at 18° C.

*Fragrance.*—None.

Plant:

*Foliage.*—Shape: Kidney-shape, with open cordate base, weak lobes, outline fairly uniformly rounded. Texture Upper surface slightly velvety. Margin: Bicrenated. Size of leaf: 76 mm wide, 45–50 mm long. Color of upper surface: Medium-green, approximately RHS 137 B to RHS 137 C. Color of zonation: Weak, brown, about RHS 166 A. Petiole: 55–65 mm in length, 3 mm in diameter, about RHS 144A.

*General appearance and form.*—Internode length: 5–15 mm. Branching pattern: 6.1 branches. Plant size: 16.5 cm high as measured from the base of the stem/soil surface to the surface of the foliage canopy and 33.0 cm wide.

Disease/pest resistance/susceptibility: None observed to date.

I claim:

1. A new and distinct cultivar of geranium plant named 'Fispurple', as described and illustrated.

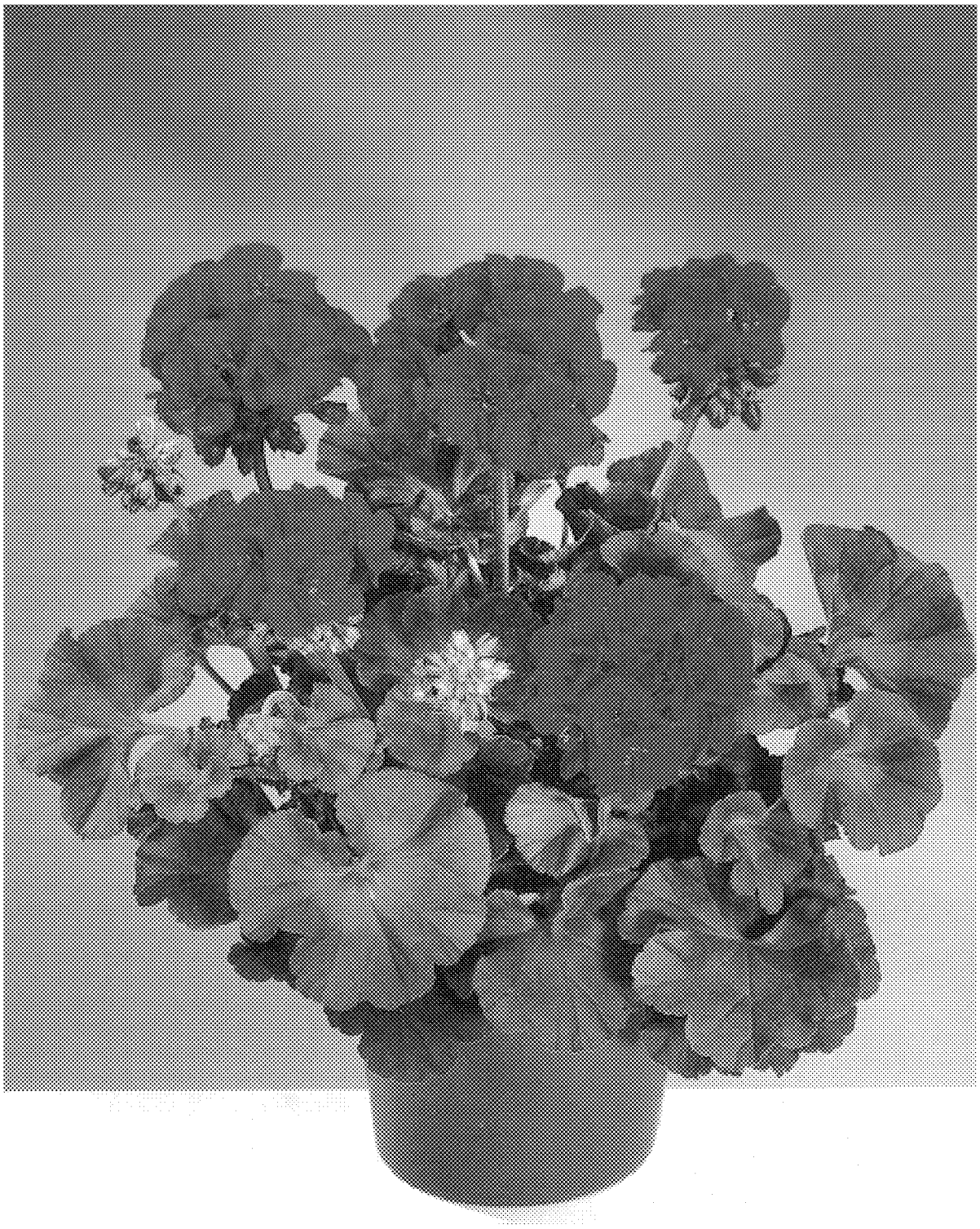

* * * * *